United States Patent
Massoni et al.

(10) Patent No.: US 11,701,308 B2
(45) Date of Patent: Jul. 18, 2023

(54) COMPOSITIONS FOR COLORING HAIR INCLUDING ULTRA-EFFICIENT HIGH AQUEOUS, MULTI-LAMELLAR EMULSION SYSTEMS, AND METHODS OF MAKING THE SAME

(71) Applicant: Combe Incorporated, White Plains, NY (US)

(72) Inventors: Jack Massoni, New Fairfield, CT (US); Padmaja Prem, White Plains, NY (US); Joanne Shkreli, Carmel, NY (US)

(73) Assignee: COMBE INCORPORATED, White Plains, NY (US)

( * ) Notice: Subject to any disclaimer, the term of this patent is extended or adjusted under 35 U.S.C. 154(b) by 0 days.

(21) Appl. No.: 16/818,882

(22) Filed: Mar. 13, 2020

(65) Prior Publication Data

US 2021/0283024 A1    Sep. 16, 2021

(51) Int. Cl.
  *A61K 8/04* (2006.01)
  *A61K 8/55* (2006.01)
  *A61K 8/92* (2006.01)
  *A61Q 5/00* (2006.01)
  *A61Q 5/10* (2006.01)

(52) U.S. Cl.
  CPC .............. *A61K 8/042* (2013.01); *A61K 8/55* (2013.01); *A61K 8/92* (2013.01); *A61Q 5/004* (2013.01); *A61Q 5/10* (2013.01); *A61K 2800/4324* (2013.01); *A61K 2800/5422* (2013.01)

(58) Field of Classification Search
  CPC . A61K 8/042; A61K 8/92; A61K 8/55; A61K 2800/5422; A61K 2800/4324; A61Q 5/004; A61Q 5/10
  See application file for complete search history.

(56) References Cited

U.S. PATENT DOCUMENTS

| | | | |
|---|---|---|---|
| 6,077,816 A | 6/2000 | Puvvada et al. | |
| 7,419,510 B2 | 9/2008 | Massoni | |
| 7,608,116 B2 | 10/2009 | Nicolas-Morgantini et al. | |
| 7,754,775 B2 | 7/2010 | Mercier et al. | |
| 9,237,993 B2* | 1/2016 | Massoni | A61K 8/602 |
| 9,358,190 B2 | 6/2016 | Kim et al. | |
| 9,474,704 B2 | 10/2016 | Massoni et al. | |
| 10,022,312 B2 | 7/2018 | Massoni et al. | |
| 2002/0015685 A1 | 2/2002 | Pascual et al. | |
| 2005/0238677 A1 | 10/2005 | Mercier et al. | |
| 2005/0283925 A1* | 12/2005 | Glenn | A61K 8/411 8/405 |
| 2007/0209124 A1 | 9/2007 | Bureiko et al. | |
| 2018/0092816 A1 | 4/2018 | Perricone et al. | |

FOREIGN PATENT DOCUMENTS

| | | |
|---|---|---|
| DE | 10 2006 015544 A1 | 10/2007 |
| EP | 1832273 A1 | 9/2007 |
| KR | 10-2016-0045000 A | 4/2016 |
| KR | 10-2018-0079501 A | 7/2018 |
| WO | 01/85108 A2 | 11/2001 |
| WO | 2015/112787 A1 | 7/2015 |

OTHER PUBLICATIONS

International Search Report and Written Opinion in counterpart PCT Application No. PCT/US2021/021817, dated Jun. 28, 2021 (16 pages).

* cited by examiner

*Primary Examiner* — Snigdha Maewall
(74) *Attorney, Agent, or Firm* — Venable LLP

(57) ABSTRACT

This disclosure relates to a composition for coloring hair containing comprising a multi-lamellar gel emulsion, which includes a haircolor formulation, and a method of making the same. The multi-lamellar gel emulsion includes about 0.5 wt % to about 4.0 wt % of cosmetically acceptable emulsifying fats, a cosmetically acceptable non-ionic surfactant, a water-soluble suspending polymer, and at least 80 wt % of water.

21 Claims, 4 Drawing Sheets

COMPOSITIONS FOR COLORING HAIR INCLUDING ULTRA-EFFICIENT HIGH AQUEOUS, MULTI-LAMELLAR EMULSION SYSTEMS, AND METHODS OF MAKING THE SAME

BACKGROUND OF THE INVENTION

Early haircoloring compositions, in particular vehicles for two-part oxidative coloring systems, contained high levels of organic solvents in combination with low HLB (hydrophilic/lipophilic balance) surfactants. Typically, the water content of the dye bases is under 30 wt %. When mixed with the developer, which contained an oxidant, typically hydrogen peroxide, and high percentages of water, the surfactants would precipitate from solution in the form of a gel. This gel was an acceptable carrier of dyes and developer actives, as it allowed for rapid penetration of dyes into the hair, while providing sufficient viscosity and rheological properties so that the composition remains stay put on a consumer's hair without dripping during processing times of up to one hour or more.

The high organic solvent/low water haircolor vehicles are very easy to manufacture, as they dominated the permanent haircolor market through the 1980s. A significant drawback with these types of compositions is the inefficiencies of the dye system. When compared to more advanced haircoloring systems with a higher water content, the high organic solvent/low water haircolor could use up to twice as much (wt %) dye precursors in order to achieve the same degree of coloration and gray coverage.

Haircoloring systems with a higher water content became more popular as alkali swellable polymers were commercialized, which were now stable in hydrogen peroxide. Materials marketed under the Aculyn™ and Structure™ brand names could be added to the developer portion of the permanent haircolor system and maintain their integrity for an extended shelf life. Under acid pH conditions, the polymers would remain un-cross linked, keeping the composition thin and easily pourable. Once mixed with the dye portion, that normally has an alkaline pH, the increase in pH would cause the mixture to instantly thicken. Using the anionic polymer in this manner would allow the formulator to create dye phases with higher levels of water, and little to no surfactants, solvents, or other materials that contribute to the mixtures' viscosity and structure.

When it is desirable to start with a dye phase that already has some viscosity, U.S. Pat. No. 7,419,510 describes a composition where a traditional water-soluble anionic polymer is used in the dye phase. The developer requires a specific concentration of secondary ethoxylated fatty alcohols at a required HLB range. When combined, a high aqueous dye system is maintained, resulting in an appropriate mixture viscosity and flow properties.

Many professional haircoloring brands have haircolor systems with higher water contents than the high organic solvent/low water haircolor. However, these systems may use 10-20 wt % fatty alcohols and emulsifiers to create heavy crèmes and crème/gel colorants. These are most suitable for bowl and brush application.

Embodiments of haircolor systems with higher water content use the dye precursors more efficiently, although with some degree of variability depending upon the exact composition and desired results. Besides efficient use of dye precursors, these haircoloring systems can be milder, provides less staining, and less likely to produce an adverse reaction with a user of the product, as compared to traditional compositions.

SUMMARY OF THE INVENTION

To improve hair coloration dye efficiency, gray coverage and depth of color, provided herein is a composition for coloring hair and covering gray comprising a multi-lamellar gel emulsion (gel MLE), which comprises: (a) a haircolor formulation; (b) at least two cosmetically acceptable emulsifying fats; (c) a cosmetically acceptable non-ionic surfactant; (d) a water-soluble suspending polymer; and (e) water.

For example, the multi-lamellar gel emulsion (gel MLE) may contain: (a) a haircolor formulation; (b) at least two cosmetically acceptable emulsifying fats at a content of about 0.5 wt % to about 4.0 wt %; (c) a cosmetically acceptable non-ionic surfactant; (d) a water-soluble suspending polymer; and (e) at least 80 wt % of water.

DETAILED DESCRIPTION OF THE INVENTION

Figure 1:
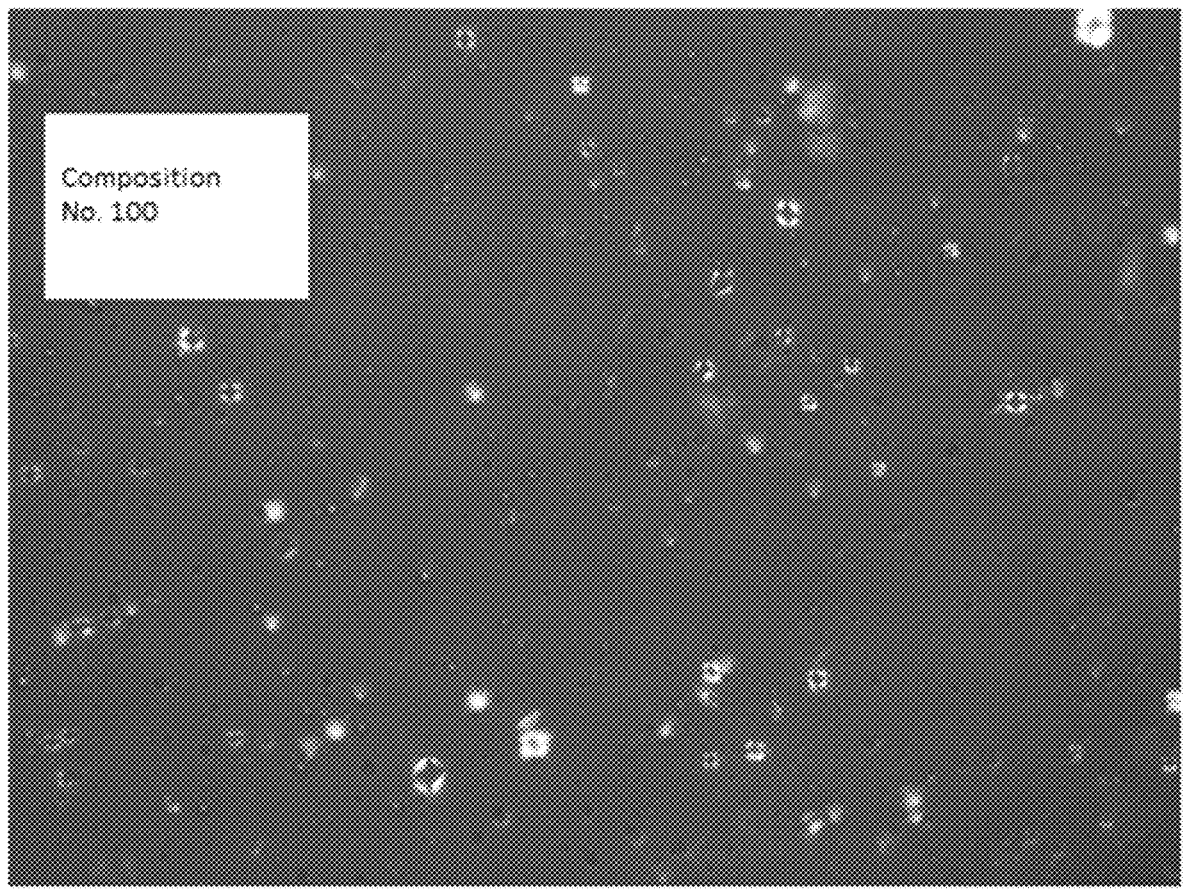
FIG. 1 is a polarized light microscope image of a haircolor formulation, in a light brown shade, in accordance with the present invention.

This disclosure provides compositions for coloring hair and covering gray that further improves the efficiency of high aqueous vehicles by including a low level of cosmetically acceptable emulsifying fats, and a cosmetically acceptable non-ionic surfactant in addition to a cosmetically acceptable water-soluble suspending polymer to produce a multi lamellar gel emulsion (gel MLE or gel network).

The cosmetically acceptable emulsifying fat(s) is a combination of at least two fatty materials with an appropriate HLB range of about 4 to about 9, or about 5 to about 9, to allow for the formation of the multi lamellar gel emulsion. In particular, the gel MLE with the high water content provides improved stability and effectiveness of delivery of hair color components into hair. Given the level of water in the system, the present disclosure pertains to oil-in-water type emulsions.

Stabilization of hair dyes while optimizing the efficiency of the carrier can be challenging due to the susceptibility of the dyes to oxidation. However, with a multi lamellar gel emulsion, properties including consumer pleasing aesthetics such as a texture, decreased staining and increased stability of product during storage (i.e., reduced premature oxidation) can be achieved. It is believed that, emulsifying fats can form bilayers and may be employed in compositions for coloring hair to reduce or prevent dye staining of skin or other surfaces, providing enhanced protection against premature oxidation of the colorant, improving the stability of the dyes, and creating maximum dye delivery into hair. During application of the haircolor composition, or product, the mechanical action breaks the sheer thinning structure of the multi-lamellar gel emulsion (gel MLE) allowing an effective and controlled delivery of actives inside the hair fiber and providing enhanced color delivery, gray coverage and reduced skin/scalp staining.

An MLE may have a liquid crystalline structure or gel lamellar network structure. Liquid crystalline MLEs have been described in, for example, U.S. Pat. No. 7,754,775. The hair coloring compositions described in WO 2015/112787 also have a liquid crystalline MLE. The use of liquid crystalline MLE results in a haircoloring composition that is opaque and has a crème consistency.

In contrast, the MLE in the presently described haircoloring composition is not a liquid crystalline MLE, but is a gel MLE, which has the consistency of a gel rather than a crème. A haircoloring formulation with a gel MLE is generally more transparent or translucent compared to a crème formulation with a liquid crystalline MLE.

The gel MLE generally requires less fat than a liquid crystalline MLE. The higher amount of fats present in liquid crystalline MLEs can have adverse effects, including a less efficient haircoloring composition, as the crème formulation does not allow efficient penetration of dye precursors into the hair.

The gel MLE allows better penetration of dyes into hair and thus better coloring results and gray coverage can be achieved. As a result, the compositions provided herein allow for significant reduction in dye concentration when compared to the most efficient high aqueous vehicles in commercial use. The effect is more pronounced with compositions that are designed for shorter dwell times of 5 to 10 minutes.

Figure 2:
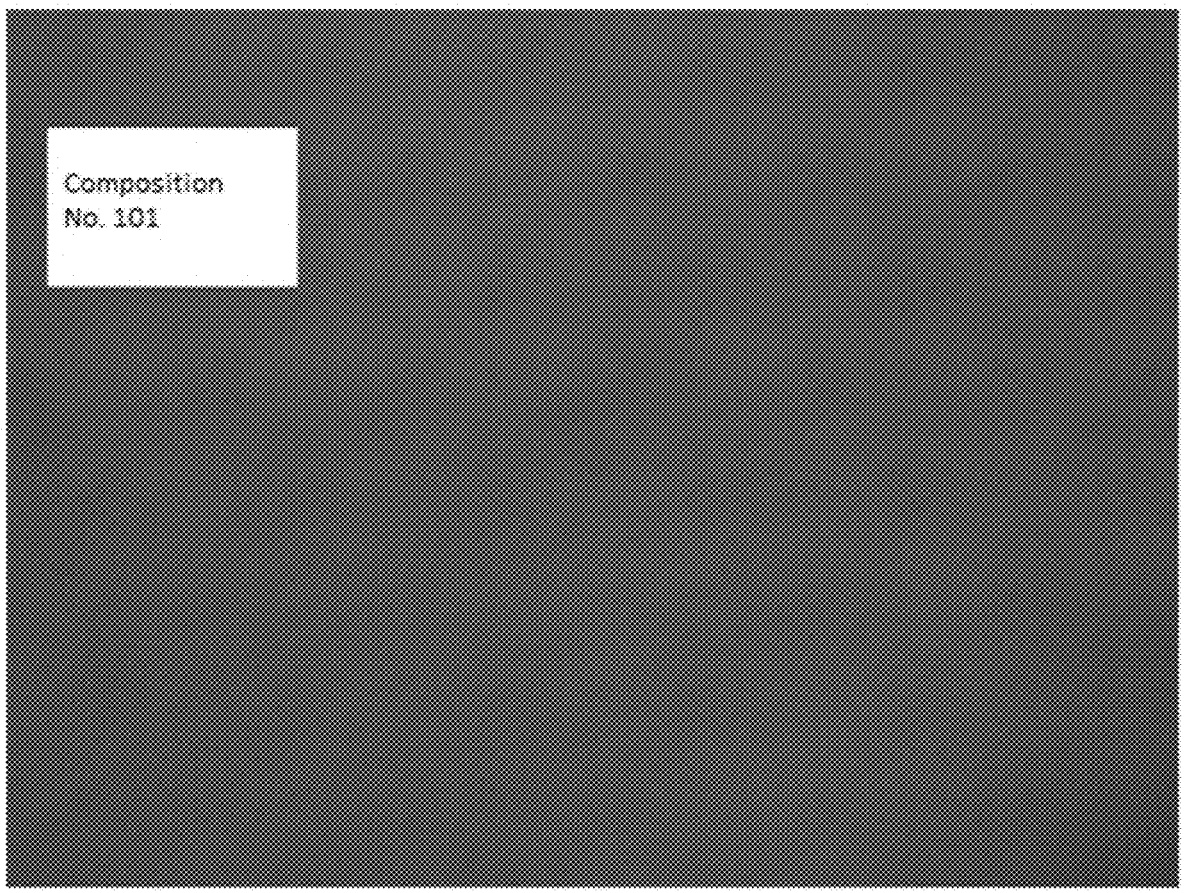
FIG. 2 is a polarized light microscope image of a haircolor formulation, in a light brown shade, without emulsifying fats.
Figure 3:
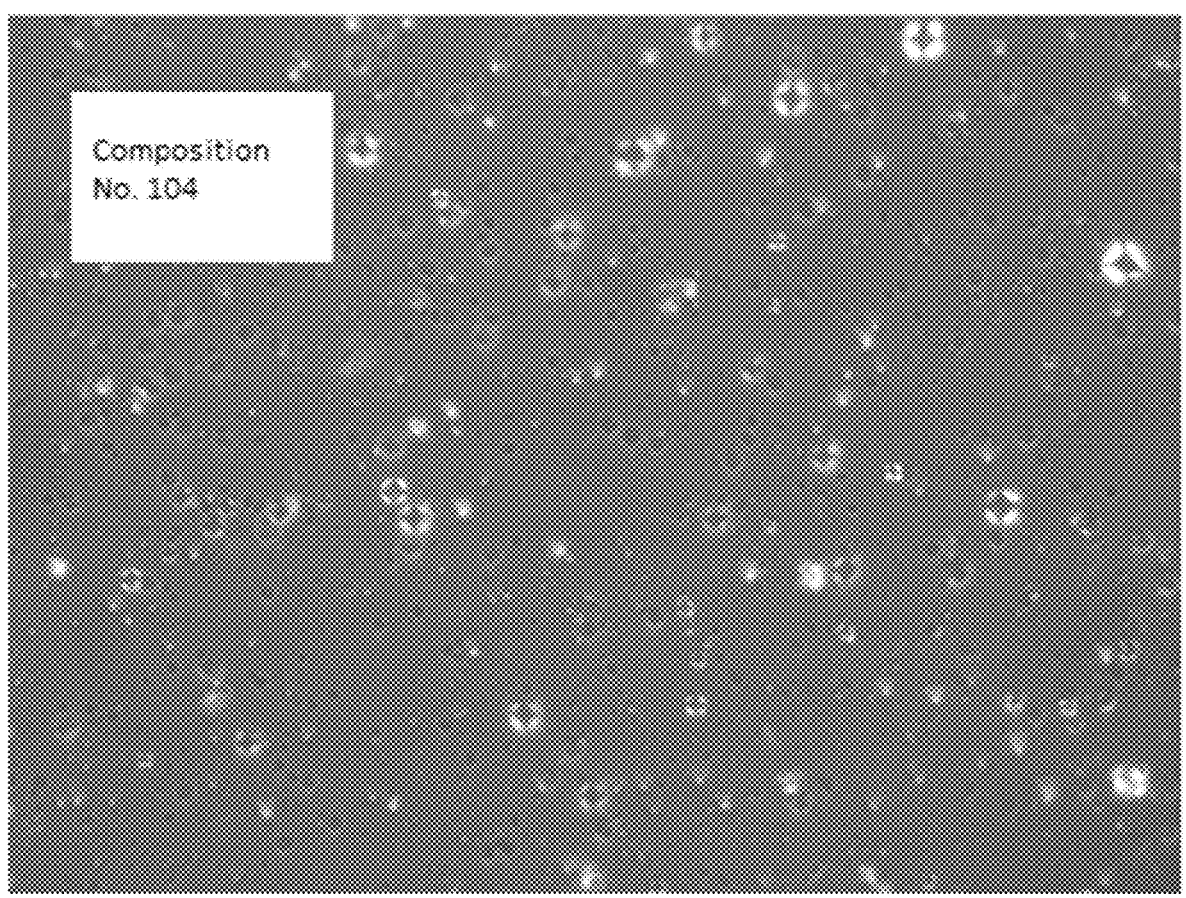
FIG. 3 is a polarized light microscope image of a haircolor formulation, in a black shade, in accordance with the present invention.
Figure 4:
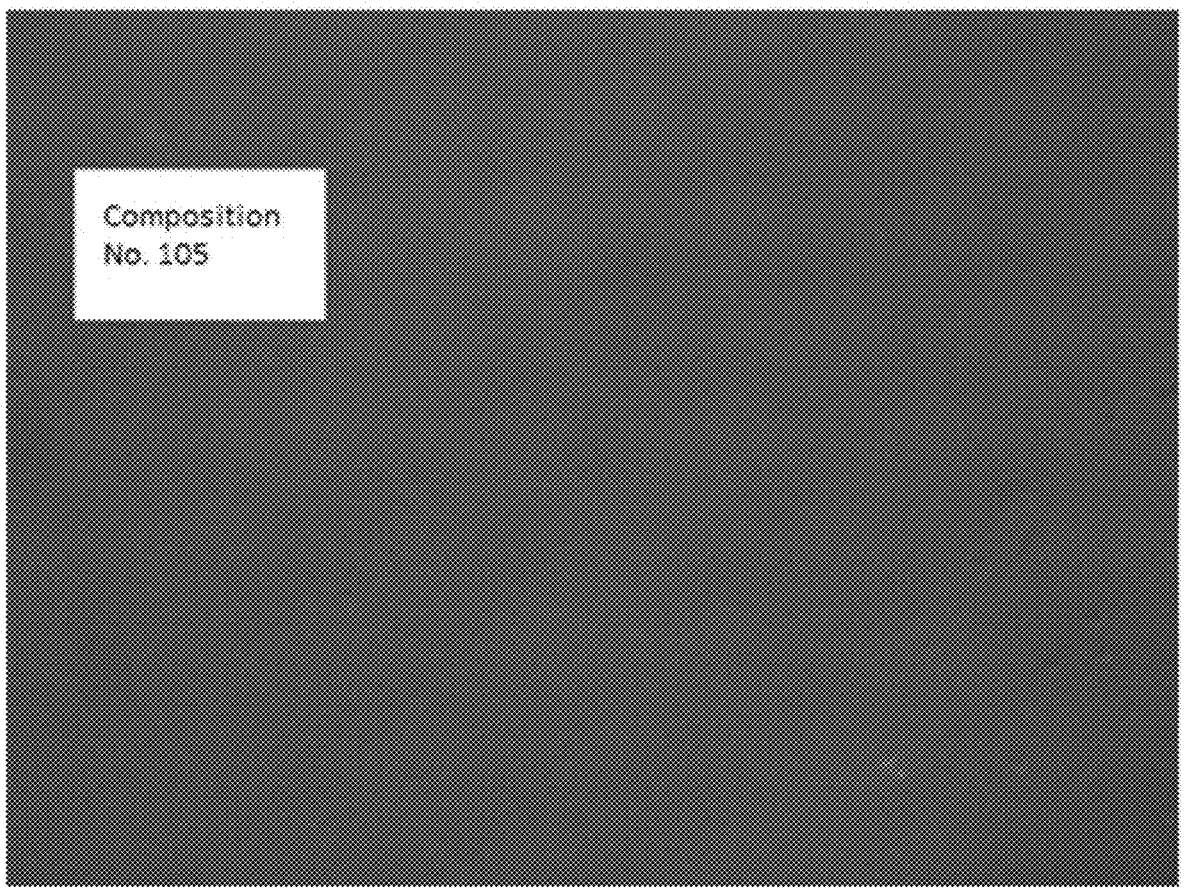
FIG. 4 is a polarized light microscope image of a haircolor formulation, in a black shade, without emulsifying fats.

Without wishing to be bound by a particular theory, it is believed that the ultra-efficient effect is due to improved delivery of dye precursors from the gel MLE; however, this is negated when the composition contains a higher more typical level of emulsifying fats, even if an MLE is formed. In this instance, the increased percentage of materials and the cream rheology of the vehicle hinders dye penetration into hair and are not available for deposition into the hair. As the cosmetically acceptable emulsifying fat(s) are at such a low level in the formula, they can be suspended by thickening the composition with a cosmetically acceptable water-soluble suspending polymer. To form a multi-lamellar gel emulsion, the total HLB of the composition is from about 4 to about 9, or about 5 to 9. The presence of the gel MLE structure may be confirmed, for example, by viewing a sample under a light microscope at a magnification level of 400 through a polarized light filter. Specifically, the presence of light bursts, which resemble a "maltese cross" pattern, would be visible upon such examination. For instance, in FIGS. 1 and 3, which correspond to Compositions 100 and 104 (Table 1), light bursts are clearly present. If the cosmetically acceptable emulsifying fat(s), cosmetically acceptable non-ionic surfactant and water soluble polymer had not combined to form the gel MLE, no light bursts having maltese cross patterns would be visible upon microscopic review with a polarized light filter, for example, as shown in FIGS. 2 and 4, which correspond to Compositions 101 and 105 (Table 1). Without application of a polarized filter, the light bursts are not visible even if the gel MLE is formed.

In accordance with the present disclosure, at least two cosmetically acceptable emulsifying fats are used in order to achieve an HLB value of about 4 to about 9, or about 5 to about 9. A cosmetically acceptable emulsifying fat for use in accordance with the present disclosure is a material that has no charge groups in its head. For example, materials such as fatty alcohols, ethoxylated and propoxylated fatty alcohols, fatty esters, and vegetable oils can be cosmetically acceptable emulsifying fats. Non-ionic materials such as Montanov 68 (cetearyl alcohol & cetearyl glucoside) from Seppic Inc. can also be used as a cosmetically acceptable emulsifying fat. In addition, specific phosphate esters that produce a negative charge when neutralized at alkaline pH can be cosmetically acceptable emulsifying fats. Phosphate esters in accordance with the present invention may be Crodafos CES (cetearyl alcohol, dicetyl phosphate and ceteth-10 phosphate) or Crodafos CS20A (cetearyl alcohol, dicetyl phosphate and ceteth-20 phosphate) from Croda, Inc. In an embodiment, the at least two cosmetically acceptable fats are a combination of at least two phosphate esters. In an embodiment, the at least two cosmetically acceptable fats are a combination of at least a non-ionic material and a phosphate ester. Cosmetically acceptable emulsifying fats that can be used in accordance with the present disclosure also include: glycol distearate, sorbitan trioleate, propylene glycol isostearate, glycol stearate, sorbitan sisquioleate, glyceryl stearate, lecithin, sorbitan oleate, sorbitan monostearate, sorbitan stearate, sorbitan isostearate, steareth-2, oleth-2, glyceryl laurate, ceteth-2, PEG-30 dipolyhydroxystearate, glyceryl stearate, Prolipid 141, isolaureth-3, cetyl alcohol, stearyl alcohol, behenyl alcohol, cetearyl alcohol, almond oil, lanolin, apricot kernel oil, borage seed oil, canola oil, castor oil, jojoba oil, olive oil, shea butter, soybean oil, behenyl alcohol, lauryl alcohol, myristyl alcohol, palmitic acid, stearic acid, sucrose cocoate, PEG-4 dilaurate, methyl glucose sesequistearate, C11-15 pareth-3, sorbitan palmitate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, sorbityl laurate, cetearyl olivate, sorbitan olivate, ceteareth-20, isolaureth-6, behenyl glucoside, stearmide MEA, PEG-100 stearate, polysorbate 85, PEG-7 olivate and combinations thereof.

The cosmetically acceptable emulsifying fat content of the composition may be about 0.5% by weight to about 4% by weight, and the added dye efficiency quickly drops off outside this range. In an embodiment, the cosmetically acceptable fat content of the composition may be about 0.5% by weight to about 3% by weight, or about 0.5% by weight to about 2% by weight, or about 0.5% by weight to about 1.5% by weight, or about 0.5% by weight to about 1% by weight, or about 1.0% by weight to about 1.5% by weight.

Cosmetically acceptable non-ionic surfactants, which are also co-emulsifying agents and viscosity builders and can be used in accordance with the present disclosure include: cetearyl glucoside, decyl glucoside, cocoglucoside, lauryl glucoside, caprylyl capryl glucoside, PEG-8 oleate, polyglyceryl-3 methylglucose distearate, oleth-10, polyoxyl 10 oleyl ether, ceteth-10, PEG-8 laurate, cocoamide MEA, polysorbate 60, isolaureth-10, polysorbate 80, isosteareth-20, PEG-60 almond glycerides, PEG-20 methyl glucose sesquistearate, ceteareth-20, oleth-20, steareth-20, steareth-21, ceteth-20, C11-15 pareth-7, C11-15 pareth-9, C11-15 pareth-30, steareth-10, steareth-100, polysorbate-20, and any combination thereof. The cosmetically acceptable non-ionic surfactants content of the composition may be about 0.1% by weight to about 2% by weight, or about 0.25% by weight to about 1% by weight, and any combination thereof.

To achieve adequate viscosity and desirable rheological properties to allow for ease of consumer application and adherence to the hair, the at least two cosmetically acceptable emulsifying fats and cosmetically acceptable non-ionic surfactant are suspended in at least one water-soluble suspending polymer. The water-soluble suspending polymer can deliver a sufficient viscosity to keep the oil phase suspended. As a result, viscosity of the product can range from about 5000 cps to about 200,000 cps, or about 10,000 cps to about 175,000 cps, or about 20,000 cps to about 150,000 cps, or about 40,000 to about 100,000 cps.

The type of water-soluble suspending polymer that may be used is not particularly limited but should be suitable for application to hair. The water-soluble suspending polymer may be selected from the group consisting of: nonionic, anionic, cationic, or amphoteric polymer, a saturated or unsaturated long chain fatty acid, carboxymethylcellulose, sodium alginate, a cross-linked homopolymer of acrylic acid or of acrylamidopropanesulfonic acid or associative polymer, carbomers, including but not limited to Carbopol Ultrez 10, hydroxyethyl cellulose, hydroxypropyl cellulose, guar gum, xanthan gum, scleroglucan gum, quaternized versions of hydroxyethyl cellulose, hydroxypropyl cellulose, guar gum, scleroglucan gum, polyquaternium-10, polyquaternium-7, polyquaternium-11, guar hydroxypropyltrimonium Chloride, hydroxypropylmethylcellulose, carboxymethylhydroxyethyl cellulose, carboxymethylhydroxypropyl guar, or any combination thereof.

This water-soluble suspending polymer is a part of the gel MLE system. The water-soluble suspending polymer content of the composition may be about 0.1% by weight to about 2% by weight, or about 0.3% by weight to about 1.7% by weight, or about 0.5% by weight and 1.5% by weight and any combination thereof. As noted above, viscosity may be adjusted to the preferred range depending on the desired method of application.

An embodiment of the disclosure is a composition for coloring hair comprising a multi-lamellar gel emulsion, wherein the multi-lamellar gel emulsion comprises: (a) a haircolor formulation; (b) at least two cosmetically acceptable emulsifying fats; (c) a cosmetically acceptable non-ionic surfactant; (d) a water-soluble suspending polymer; and (e) water.

An embodiment of the disclosure is a composition for coloring hair comprising a multi-lamellar gel emulsion, wherein the multi-lamellar gel emulsion comprises: (a) a haircolor formulation; (b) at least two cosmetically acceptable emulsifying fats at a content of about 0.50 wt % to about 4 wt %; (c) a cosmetically acceptable non-ionic surfactant content of about 0.1 wt % to about 2.0 wt %; (d) a water-soluble suspending polymer; and (e) at least 80 wt % of water, or about 80 wt % to about 95 wt % of water, or about 83 wt % to about 95 wt % of water, or about 85 wt % to about 95 wt %, or about 86 wt % to about 95 wt %, or about 92 wt % to about 95 wt %.

The pH of the composition should be in a range that allows for development of color, preferably about 5 to about 12.

The multi-lamellar gel emulsion in the composition for coloring hair comprises a hair color formulation, which may be either a developer, such as hydrogen peroxide, persulfates, percarbonates, or any other developer used in a traditional two-components haircolor system or kit, or a haircolor composition. A haircolor composition as referred to herein is an aqueous composition comprising an oxidative dye, a non-oxidative dye, or any combination thereof.

Oxidation (or oxidative) dyes are a class of compounds used in traditional two-component permanent hair color systems, where the oxidative dyes undergo oxidation when mixed with an oxidant such as hydrogen peroxide. These two component kits generally comprise an alkaline composition of oxidation hair dyes in a liquid, gel or cream vehicle and developer composition that utilizes an oxidizing agent, usually hydrogen peroxide. The two compositions are mixed immediately prior to application to the hair. The alkaline pH of the resultant mixture causes the hair shaft to swell, allowing the dye precursors to penetrate into the cortex of the hair. These dye precursors are then oxidized and combine to form larger molecules. These larger molecules contain a significant level of conjugated double bonds, hence producing a colored product that is visible from the exterior of the hair. After an appropriate development time during which the composition dwells on the hair, the mixture is rinsed from the hair. The color of the hair is then permanently altered. Depending upon the pH of the mixture and the strength of the developer, these systems can either have the capability to simultaneously lighten the hair's natural pigment and deposit color, or to just deposit color.

Oxidation dye precursors are primarily aromatic compounds and typically have a low molecular weight. Oxidation dyes form the basis of hair dyes and are generally categorized under two groups: primary intermediates and couplers. Thus, the primary intermediate forms the base of a permanent hair-coloring product.

In a certain embodiment, the primary intermediate is selected from the group consisting of para-substituted benzene derivatives such as p-phenylenediamine, N,N-Bis(2-hydroxyethyl)-p-phenylenediamine sulfate, p-aminophenol, 2,4,5,6-tetraaminopyrimidine, p-toluenediamine, 2-chloro-p-phenylenediamine, N-phenyl-p-phenylenediamine, p-methylaminphenol, 1-amino-4-(2-methoxyethyl)-aminobenzene, 2-(hydroxymethyl)-p-phenylenediamine, 3-methyl-p-aminophenol, 2-(2-hydroxyethyl)-p-phenylenediamine, 4,4'-diaminodiphenylamine, 1,3-dimethyl-2,5-di aminobenzene, 2-isopropyl-p-phenylenediamine, N-(beta-hydroxypropyl)-p-phenylenediamine, 2-methyl-p-aminophenol, N-2-methoxyethyl-p-phenylenediamine, 2-hydroxyethyl-p-phenylenediamine, 2,6-dimethyl-p-phenylenediamine, 3-methyl-p-aminophenol, 2-propyl-p-phenylenediamine, 2-(2'-hydroxyethylaminomethyl)-p-aminophenol, 2-(methoxymethyl)-p-aminophenol, 2-methyl-4-dimethylaminoaniline, 5-aminosalicylic acid, 2,3-dimethyl-p-phenylenediamine, 2,6-diethyl-p-phenylenediamine, 2,5-dimethyl-p-phenylenediamine, N,N-diethyl-p-phenylenediamine, N,N-dipropyl-p-phenylenediamine, 4-amino-N,N-diethyl-3-methylaniline, 4-N,N-bis(2-hydroxyethyl)-amino-2-methylaniline, 4-N,N-bis(2-hydroxyethyl)amino-2-chloroaniline, 2-(2-hydroxyethyl)-p-phenylenediamine, 2-fluoro-p-phenylenediamine, N-(2-hydroxypropyl)-p-phenylenediamine, 2-hydroxymethyl-p-phenylenediamine, N,N-dimethyl-2-methyl-p-phenylenediamine, N-ethyl-N-(2-hydroxyethyl)-p-phenylenediamine, N-(2,3-dihydroxypropyl)-p-phenylenediamine, N-(4'aminophenyl)-p-phenylenediamine, 2-(2-hydroxyethoxy)-p-phenylenediamine, 2-(acetylaminoethoxy)-p-phenylenediamine, 2-methyl-1-N-(2-hydroxyethyl)-p-phenylenediamine, 4-methyl-o-Phenylenediamine, a salt thereof, and any combination thereof.

The haircolor composition may also comprise at least one dye coupler. The dye coupler is used for developing the shade and achieving a broader spectrum of color imparted by the haircolor composition. The dye coupler may be selected from the group consisting of meta-substituted benzene derivatives: resorcinol, 4-chlororesorcinol, 2-methylresorcinol, m-aminophenol, 1-naphthol, 1,5-naphthalenediol, 2,7-naphthalenediol, 2,4-Diaminophenol, hydroxybenzomorpholine, 1-hydroxy-3-dimethylaminobenzene, 4-amino-2-hydroxytoluene, 2-methyl-5-hydroxyethylaminophenol, 1-methoxy-2,5-diaminobenzene, phenyl methyl pyrazolone, 2,4-diaminophenoxyethanol HCl, 4-ethoxy-m-phenylenediamine, 1-hydroxy-3-amino-4,6-dichlorobenzene, 1-hydroxy-2,5-diamino-4-methoxybenzene, 4-amino-m-cresol, 6-amino-m-cresol, 2-amino-4-hydroxyethylaminoanisole, 5-amino-6-chloro-o-cresol, 6-amino-o-cresol, 4,6-bis(2-hydroxyethoxy)-m-phenylenediamine, 5-amino-4-chloro-o-cresol, 2-ethyl amino-p-cresol, 2-amino-5-acetaminophenol, 2-methyl-1-naphthol, 1-acetoxy-2-methylnaphthalene, 1-hydroxy-6-aminonaphthalene-3-sulfonic acid, thymol, 1,5-dihydroxy-1,2,3,4-tetrahydronaphthalene, 2-chlororesorcinol, N,N-bis(hydroxyethyl)-2,4-diaminophenetole, 4,6-bis(hydroxyethyl)-m-phenylenediamine, N,N-bis(hydroxyethyl)-m-phenylenediamine, 2,6-diaminotoluene, 6-hydroxybenzomorpholine, 2-hydroxy-4-hydroxyethyl aminotoluene, 4,6-dichloro-m-aminophenol, 2-methyl-m-aminophenol, 2-chloro-6-methyl-m-aminophenol, 2-hydroxyethoxy-5-aminophenol, 2-chloro-5-trifluoroethylaminophenol, 4-chloro-6-methyl-m-aminophenol, N-hydroxyethyl-4-methoxy-2-methyl-m-aminophenol, 5-amino-4-methoxy-2-methylphenol, 2-dimethylamino-5-aminopyridine, 6-methoxy-8-aminoquinoline, 2,6-dihydroxy-4-methylpyridine, 2,6-dihydroxy-3,4-dimethylpyridine, 5-chloro-2,3-dihydroxypyridine, 4-hydroxyindole, 5,6-dihydroxyindole, 7-hydroxyindole, 5-hydroxyindole, 2,3-dihydroxynaphthalene, 5-methyl-o-aminophenol, 6-methyl-o-aminophenol, 2-amino-5-acetaminophenol, 1,7-dihydroxynaphthalene, 1-hydroxy-6-aminonaphthalene-3-sulfonic acid, 2,3-dihydroxy-1,4-naphthoquinone, 3,4-methylenedioxy-1((beta-hydroxyethyl)amino) benzene, 3,4-methylenedioxyphenol, 1-methoxy-2-amino-4-((beta-hydroxyethyl)amino)benzene, 1-naphthol-4-sulfonic acid, m-phenylenediamine, 2,6-diaminotoluene, N,N-bis(hydroxyethyl)-2,4-diaminophenetole, bis(2,4-diaminophenoxy)-1,3-propane, 1-hydroxyethyl-2,4-diaminobenzene, aminoethoxy-2,4-di aminobenzene, 2,4-diaminophenoxyacetic acid, 2,4-diamino-5-methylphenetole, 2,4-diamino-5-hydroxyethoxytoluene, 2,4-dimethoxy-1,3-diaminobenzene, 2,6-bis(hydroxyethylamino)-toluene, 2-hydroxy-4-carbamoylmethylaminotoluene, 2-chloro-6-methyl-m-aminophenol, 2-hydroxyethoxy-5-aminophenol, N-cyclopentyl-3-aminophenol, N-hydroxyethyl-4-methoxy-2-methyl-m-aminophenol, 5-amino-4-methoxy-2-methylphenol, 6-methoxy-8-aminoquinoline, 5-hydroxy-1,4-benzodioxane, 3,4-methylenedioxyphenol, 4-hydroxyethylamino-1,2-methylenedioxybenzene, 2,6-dihydroxy-3,4-dimethylpyridine, and any combination thereof.

Auto-oxidation (air oxidation) dyes are a sub-class of oxidation dyes, wherein the dye undergoes self-oxidation in the presence of air without the need for mixing with a separate developer/oxidant to develop color in the hair. The air oxidation dyes and primary intermediates in combination upon application to hair rapidly oxidize upon exposure to atmospheric oxygen to make coupling products to impart color to hair. The most effective air oxidation products are those that use a transition metal salt to catalyze the air oxidation reaction. These compositions are able to obtain similar gray coverage to formulas that are mixed with hydrogen peroxide.

In a certain embodiment, the air oxidation precursors are selected from the group consisting of: 1,2,4-benzenetriol, 2,4,5-trihydroxytoluene, pyrogallol, 2,5-dihydroxyanisole, 3,4-Diaminophenol, 3,4-Diaminoanisole, 5,6-dihyoxy indole and its derivatives, 5,6-dihydroxy indoline and its derivatives, 2-hydroxy-p-phenylenediamine, N-methyl-2-hydroxy-p-phenylenediamine, N,N-dimethyl-2-hydroxy-p-pheneylenediamine, 2-methoxy-p-phenylenediamine, 2,4-diaminophenol, 2,4-diaminoanisole, 3,4-dihydroxyanisole, 4-amino-2-hydroxyphenol, 2-methoxy-4-aminophenol, 2-hydroxy-4-aminoanisole, 2-amino-4-hydroxyphenol, 2-amino-4-methoxyphenol, 2-amino-4-hydroxyanisole, 2-amino-p-phenylenediamine, 2,4-dihydroxyaniline, 3-methoxy-4-aminophenol, and similar compounds with N substituted alkyl groups such as: methyl, ethyl, propyl, methanol, ethanol, isopropanol, and any combination thereof.

Non-oxidative dyes are dyes (colored molecules) that may be directly applied to hair to attain semi-permanent color. Non-limiting examples of non-oxidative dyes include: Acid yellow 1, disperse red 17, basic brown 17, acid black 1, 4-nitro-o-phenylenediamine, picramic acid, HC red 13, N,N'-bis(2-hydroxyethyl)-2-nitrop-phenylenediamine, HC red 7, HC blue 2, HC yellow 4, HC yellow 2, HC orange 1, HC red 1, HC red 3, 4-amino-3-nitrophenol, 2-hydroxyethylamino-5-nitroanisole, 3-nitro-p-hydroxyethylaminophenol, 3-methylamino-4-nitrophenoxyethanol, 2-nitro-5-glyceryl methylaniline, HC violet 1, HC orange 2, HC yellow 9, 4-nitrophenyl aminoethylurea, HC red 10, HC red 11, 2-hydroxyethyl picramic acid, HC blue 12, hydroxyethyl-2-nitro-p-toluidine, HC blue 11, HC yellow 7, HC yellow 10, 4-amino-2-nitrophenyl-amine-2'-carboxylic acid, 2-chloro-6-ethylamino-4-nitrophenol, HC violet 2, 2-amino-6-chloro-4-nitrophenol, HC yellow 13, 2,6-diamino-3-((pyridine-3-yl)azo) pyridine, basic orange 69, N-(2-nitro-4-aminophenyl)-allylamine, Basic violet 2, basic red 51, basic yellow 87, basic orange 31, HC blue 16, basic red 76, basic brown 16, basic yellow 57, acid orange 7, acid red 33, acid yellow 23, acid blue 9, acid red 92, acid yellow 3, basic blue 99, acid violet 43, disperse violet 1, acid blue 62, disperse black 9, hydroxyanthrquinoneaminopropylmethyl morpholinium methosulfate, lawsone, henna, hc blue 14, curry re, acid red 18, acid red 52, acid green 25, and disperse blue 377.

In a certain embodiment, the composition for coloring hair further comprises at least one agent known for use in haircolor compositions. One or more of these agents may be added to enhance the formation of the gel MLE or improve other beneficial properties, such as rheology, softening, or conditioning effect. The agent may include: a conditioning agent, an alkalizer, a moisturizer, a catalyst, a cationic surfactant, a polymer, or any combination thereof.

Any suitable conditioning agent may be used. In a certain embodiment, the conditioning agent is selected from the group consisting of: quaternized gum, quaternized polymer, quarternary ammonium salt, synthetic oil, plant oil, natural or synthetic wax, silicone, fatty amine, cationic and aminofunctional polysiloxane, quarternized protein, quarternized polysaccharide, polyamine, polyaminoamide, cationic cellulose, quaternary polymer of vinyl pyrrolidone and vinylimidazole, polyalkylenimine, and any combination thereof. The conditioning agent content of the composition may be about 0.1% by weight to about 2% by weight, as to maintain the high aqueous integrity of the composition.

The alkalizer may be organic or inorganic. In a certain embodiment, the alkalizer is selected from the group consisting of: ethanolamine, triethanolamine, aminomethyl propanol, ammonium hydroxide, carbonates, bicarbonates, isopropanolamine, propan-1,3-diamine, oxyethylenated and oxypropylenated hydroxyalkylamine and ethylenediamine, polyamine, sodium and potassium hydroxide, alkalisilicate, alkali metasilicate, and any combination thereof. The alkalizer content of the composition may be about 0.01% by weight to about 10% by weight, or about 0.1% by weight to about 7% by weight, or about 0.5% by weight to about 5% by weight, and any combination thereof.

Any moisturizer for application to hair may be added to the compositions disclosed herein. For example, the moisturizer may include humectants, occlusive, and emollients. The moisturizer may be selected from the following group: dimethicone, petrolatum, paraffin, lanolin, natural oils, mineral oil, glycerin, sorbitol, sodium hyaluronate, hyaluronic acid, urea, propylene glycol, alpha hydroxyacids, sugars, propanediol, ceramides, 1,2,6-hexanetriol, butylene glycol, dipropylene glycol, hexylene glycol, panthenol, phytantriol, inositol, hexanediol, hydrolyzed silk, hydrolyzed keratin, erythritol, capryl glycol, squalene, cocoa butter, shea butter, lecithin, and beeswax. The moisturizers content of the composition may be about 0.01% by weight to about 2% by weight, or about 0.1% by weight to about 1.7% by weight, and any combination thereof.

A catalyst may be used with air oxidation dyes. A catalyst may be a water soluble salt of transition metals such as copper, cobalt, zinc, silver, nickel and/or iron. In another embodiment, the catalyst is a metal, a metal salt and/or a metal complex, wherein the metal is selected from the group consisting of: manganese, copper, cobalt, zinc, silver, nickel, chromium, vanadium, molybdenum, osmium, ruthenium, rhodium, palladium, platinum, cadmium, iron, and any combination thereof. The salt may be selected from the group consisting of: sulfate, chloride, nitrate, carbonate, phosphate, fumarate, citrate and/or tartrate. In an embodiment, the catalyst is a manganese salt. The catalyst content may be about 0.01% to about 1.0% by weight, or about 0.05% to about 0.5% by weight, or about 0.1% to about 0.4% weight, and any combination thereof.

Cationic surfactants may be used in a composition in accordance with the present disclosure. These cationic surfactants may be selected from the group including: behentrimonium chloride, behentrimonium methosulfate, benzalkonium chloride, cetrimonium chloride, cinnamidopropyltrimonium chloride, cocotrimonium chloride, dicetyldimonium chloride, dicocodimonium chloride, dihydrogentaed tallow dimethylammonium chloride, hydrogenated, palm trimethylammonium chloride, laurtrimonium chloride, quaternium-15, quaternium-18, bentonite quaternium-18, quaternium-22, stearalkonium chloride, tallowtrimonium chloride, tricetyldimonium chloride, myristylmethylammmonium bromide, cetyltrimethylammonium bromide, olealkonium chloride, isostearamidopropyl ethyldimonium ethosulfate & PEG-9, and any combination thereof. Cationic surfactant content of the composition may be about 0.1% by weight to about 2% by weight.

Any other ingredients known for use in the art in the formulation of haircolor compositions may also be added to the composition in accordance with this disclosure, including but not limited to at least one opacifier, such as glycol stearate, stearamide AMP, at least one preservative, such as a paraben type preservative, at least on fragrance, at least one chelating agent, at least one antioxidant, and/or at least one hair regrowth active ingredient.

A chelating agent may be added to increase the stability of the product by decreasing the presence of metal ions, which otherwise, if present, might cause damage to or undesirably color the hair. The chelating agent may be selected from the group consisting of: EDTA, a sodium salt of EDTA, HEDTA, etidronic acid, citric acid, aminopolycarboxylic acid, 2,3-dihydroxybenzoic acid, dimercaptosuccinic acid, iminodiacetic acid, gluconic acid, trisodium citrate, and any combination thereof. The chelating agent content of the composition may be about 0.01% by weight to about 1%.

The antioxidant content in the composition may be adjusted to delay the onset of color for stability reasons, or to minimize potential staining of the skin, or simply added in small amounts to increase the absorption of the dye on the hair. When used, the antioxidant content may be about 0.02% to about 1% by weight of the composition. Increasing the antioxidant content further may result in poor color deposition in the hair. Any antioxidant or reducing agent, or combination thereof, may be used, including, but not limited to, sodium sulfite, bisulfite salt, thioglycolate salt, erythorbic acid, etidronic acid, ascorbic acid, thiosulfate salt, ascobylated compounds, cysteine, sodium hydrosulfite, thiourea, thiolactic acid, glyceryl monothiolgycolate, thioglycerol, 2,5-dihydroxybenzoic acid, zinc formosulfoxylate, and any combination thereof.

Another embodiment of the disclosure is a method of making a composition for coloring hair comprising a multi-lamellar gel emulsion. This method comprises the steps of, a) heating a formulation comprising water to obtain heated water, where the dyes, antioxidants, and chelating agents are dissolved, b) dispensing the water-soluble suspending polymer in the water phase, c) mixing the cosmetically acceptable emulsifying fat(s) in the hot water/polymer phase, d) simultaneously cooling and homogenizing the mixed and heated formulation to obtain the haircolor composition in a multi-lamellar gel emulsion.

Homogenization as used herein is a process of breaking up oil and water systems to make a fine emulsion using a high speed, high sheer device. While use of the homogenizer in the heating step of the present disclosure is optional, to ensure successful formation of an MLE in accordance with the present disclosure, homogenization should be used during the cooling step. It was found that without incorporating homogenization during the cooling step, the MLE did not form. Any homogenizer, i.e., the device for achieving high speed and high sheer, that can perform the above-mentioned process may be used. For instance, one such homogenizer is the Olsa MAXILAB.

In the cooling step, the mixed and heated formulation is cooled from a temperature well above the melting point of the cosmetically acceptable emulsifying fat(s), to a temperature below the melting point of each of these.

The terms used in connection with this embodiment have the same meaning as the terms have with respect to the embodiments mentioned above.

EXAMPLES

Specific embodiments of the invention will now be demonstrated by reference to the following examples. It should be understood that these examples are disclosed solely by way of illustrating the invention and should not be taken in any way to limit the scope of the present invention.

Example 1

High aqueous haircolor compositions, with and without cosmetically acceptable emulsifying fats. Haircolor Compositions of a two component haircolor system comprising a low level of fats (and gel MLE) were prepared using the ingredients set forth in Table 1.

TABLE 1

| | Light brown shade with emulsifying fats No. 100 (wt %) | Light brown shade with no emulsifying fats No. 101 (wt %) | Med Brown with emulsifying fats No. 102 (wt %) | Med Brown with no emulsifying fats No. 103 (wt %) | Black shade with emulsifying fats No. 104 (wt %) | Black shade with no emulsifying fats No. 105 (wt %) |
|---|---|---|---|---|---|---|
| Water | 80-95% | 80%-95% | 80%-95% | 80%-95% | 80%-95% | 80%-95% |
| Carbomer | 0.7%-1.0% | 0.7%-1.0% | 0.7%-1.0% | 0.7%-1.0% | 0.7%-1.0% | 0.7%-1.0% |
| Antioxidants | 0.10%-3.0% | 0.10%-3.0% | 0.10%-3.0% | 0.10%-3.0% | 0.10%-3.0% | 0.10%-3.0% |
| p-phenylenediamine | 0.34% | 0.34% | 0.567% | 0.567% | 3.42% | 3.42% |
| m-aminophenol | 0.12% | 0.12% | 0.258% | 0.258% | 2.16% | 2.16% |
| p-aminophenol | 0.13% | 0.1% | 0.218% | 0.218% | 0.30% | 0.300% |
| Resorcinol | 0.37% | 0.370% | 0.756% | 0.756% | 2.25% | 2.2% |
| N,N-Bis(2-Hydroxyethyl)PPD sulfate | 0.03% | 0.03% | 0.184% | 0.184% | 0.54% | 0.54% |
| 2,4-diaminophenoxyethanol HCL | 0.00% | 0.00% | 0.00% | 0.00% | 0.63% | 0.63% |
| Cosmetically Acceptable Emulsifying fat | 0.5%-4.0% | 0.00% | 0.5%-4.0% | 0.0% | 0.5%-4.0% | 0.0% |
| Cosmetically Acceptable Non-Ionic Surfactant | 0.1%-2.0% | 0.5% | 0.1%-2.0% | 0.5% | 0.1%-2.0% | 0.5% |
| Fragrance | 0.5%-1.0% | 0.5%-1.0% | 0.5%-1.0% | 0.5%-1.0% | 0.5%-1.0% | 0.5%-1.0% |
| Alkalizer | 1.0%-4.0% | 1.00%-4.0% | 1.0%-4.0% | 1.0%-4.0% | 1.0 %-4.0% | 1.0%-4.0% |

The above haircolor compositions were mixed 1:1 with a commercial crème developer, and dyed out on 90% gray hair (human from IHIP) separately for 5 minutes, 10 minutes and 20 minutes. The resulting color of the swatches was measured using a Hunterlab Ultra Scan Colorimeter (L a b color scale). The L value ranges from 0 to 100, which represents the color intensity, where L=100 is white and L=0 is black. "a" and "b" values have no numerical limits. +a is red and −a is green, +b is yellow and −b is blue. A delta "L" of 0.5 or greater is visible to the human eye. It was found that an inclusion of a small amount of cosmetically acceptable emulsifying fats (that produce a gel MLE) into an already efficient haircolor system, will boost color delivery significantly with a change in color depth (L value) of up to 7.7 units (Table 2). This improved efficiency is most apparent with short dwell times (e.g., 5-10 minutes), but is also visible at a 20-minute dwell time.

TABLE 2

L a b values of colored swatches after 5 min of coloring using the various formulations

| 5 minute dyeouts | "L" | "a" | "b" | Delta L |
|---|---|---|---|---|
| Lt brown with fats, No. 100 | 35.9 | 5.0 | 9.8 | |
| Lt. brown no fats, No. 101 | 40.1 | 4.1 | 9.8 | 4.2 |

TABLE 2-continued

L a b values of colored swatches after 5 min of coloring using the various formulations

| 5 minute dyeouts | "L" | "a" | "b" | Delta L |
|---|---|---|---|---|
| Med. Br. with fats, No. 102 | 29.7 | 4.9 | 8.3 | |
| Med. Br. no fats, No. 103 | 37.4 | 4.1 | 9.6 | 7.7 |
| Black, with fats, No. 104 | 17.7 | 0.5 | 0.3 | |
| Black, no fats, No. 105 | 21.2 | 1.3 | 0.5 | 3.5 |

Example 2

High aqueous haircolor compositions, with and without cosmetically acceptable emulsifying fats. Haircolor Compositions of a single component haircolor system, with air oxidation dyes (e.g., no mixing with a developer), comprising a low level of fats (and gel MLE) were prepared using the ingredients set forth in Table 3.

TABLE 3

| | Light brown shade with emulsifying fats No. 106 (wt %) | Light brown shade with no emulsifying fats No. 107 (wt %) | Black shade with emulsifying fats No. 110 (wt %) | Black shade with no emulsifying fats No. 111 (wt %) |
|---|---|---|---|---|
| Water | 80%-95% | 80%-95% | 80%-95% | 80%-95% |
| Water Soluble Suspending Polymer | 1.0%-3.0% | 1.0%-3.0% | 1.0%-3.0% | 1.0%-3.0% |

TABLE 3-continued

| | Light brown shade with emulsifying fats No. 106 (wt %) | Light brown shade with no emulsifying fats No. 107 (wt %) | Black shade with emulsifying fats No. 110 (wt %) | Black shade with no emulsifying fats No. 111 (wt %) |
|---|---|---|---|---|
| Antioxidants | 0.2%-0.5% | 0.2%-0.5% | 0.2.%-0.5% | 0.2.%-0.5% |
| p-phenylenediamine | 0.52% | 0.52% | 1.0% | 1.0% |
| m-aminophenol | 0.46% | 0.46% | 1.0% | 1.0% |
| p-aminophenol | 0.40% | 0.40% | 0.3% | 0.3% |
| 1,2,4-trihydroxybenzene | 0.55% | 0.55% | 2.5% | 2.5% |
| N,N-Bis(2-Hydroxyethyl) PPD sulfate | 0.04% | 0.04% | 0.5% | 0.5% |
| 2,4-diaminophenoxy-ethanol HCl | 0.00% | 0.00% | 0.7% | 0.7% |
| Toluene-2,5-diamine | 0.00% | 0.00% | 1.6% | 1.6% |
| 2,4,5,6-tetraamino-pyrimidine sulfate | 0.02% | 0.02% | 0.00% | 0.00% |
| 2-amino-4-hydroxyethylamino-anisole sulfate | 0.05% | 0.05% | 0.7% | 0.7% |
| Cosmetically Acceptable Emulsifying fat | 0.50%-4.0% | 0.00% | 0.50-4.0% | 0.00% |
| Cosmetically Acceptable Non-Ionic Surfactant | 0.1%-2.0% | 0.50% | 0.1%-2.0% | 0.50% |
| Conditioning agent | 0.25%-3.0% | 0.25%-3.0% | 0.25%-3.0% | 0.25%-3.0% |
| Fragrance | 0.5%-0.7% | 0.5%-0.7% | 0.5%-0.7% | 0.5%-0.7% |
| Catalyst | 0.01%-0.75% | 0.01%-0.75% | 0.01%-0.75% | 0.01%-0.75% |
| Alkalizer | 0.6% to 1.0% | 0.6% to 1.0% | 1.5% to 2.0% | 1.5% to 2.0% |

The above compositions were dyed out on 90% gray hair (human from IHIP) separately for 10 and 20 minutes. The resulting color of the swatches was recorded using a Hunterlab Ultra Scan Colorimeter. It was found that an inclusion of a small amount of emulsifying fat(s) (that produce an MLE) into an already efficient haircolor system, will boost color delivery significantly with a change in depth of L value up to 4.5 units. This improved efficiency is most apparent with short dwell times (e.g., 5-10 minutes), but is also visible at a 20-minute dwell time (Table 4).

TABLE 4

L a b values of colored swatches after 10 min of coloring using the single component formulations

| 10 minute dyeouts | "L" | "a" | "b" | Delta L |
|---|---|---|---|---|
| Lt brown with fats, No. 106 | 28.7 | 5.0 | 11.9 | |
| Lt. brown no fats, No. 107 | 33.2 | 4.8 | 13.0 | 4.5 |
| Black, with fats, No. 110 | 19.8 | 1.3 | 2.2 | |
| Black, no fats, No. 111 | 21.9 | 2.3 | 4.8 | 2.1 |

While the disclosure has been described above with reference to specific embodiments thereof, it is apparent that many changes, modification, and variations can be made without departing from the concept disclosed herein. Accordingly, it is intended to embrace all such changes, modifications, and variations that fall within the spirit and broad scope of the appended claims.

What is claimed is:

1. A composition for coloring hair, comprising a multi-lamellar gel emulsion, wherein the multi-lamellar gel emulsion comprises:
   (a) a haircolor formulation;
   (b) at least two cosmetically acceptable emulsifying fats;
   (c) a cosmetically acceptable non-ionic surfactant;
   (d) a water-soluble suspending polymer; and
   (e) water,
   wherein a cosmetically acceptable emulsifying fat content of the composition is about 0.5 wt % to about 4.0 wt %,
   wherein a cosmetically acceptable non-ionic surfactant content is about 0.1 wt % to about 2 wt %, and
   wherein a water content of the composition is at least about 80 wt %.

2. The composition of claim 1, wherein the cosmetically acceptable emulsifying fat content is about 1.0 wt %.

3. The composition of claim 1, wherein the water content is about 80 wt % to about 95 wt % of water.

4. The composition of claim 1, wherein the at least two cosmetically acceptable emulsifying fats are selected from the group consisting of: glycol distearate, sorbitan trioleate, propylene glycol isostearate, glycol stearate, sorbitan sisquioleate, glyceryl stearate, lecithin, sorbitan oleate, sorbitan monostearate, sorbitan stearate, sorbitan isostearate, steareth-2, oleth-2, glyceryl laurate, ceteth-2, PEG-30 dipolyhydroxystearate, glyceryl stearate, isolaureth-3, cetyl alcohol, stearyl alcohol, behenyl alcohol, cetearyl alcohol, almond oil, lanolin, apricot kernel oil, borage seed oil, canola oil, castor oil, jojoba oil, olive oil, shea butter, soybean oil, behenyl alcohol, lauryl alcohol, myristyl alcohol, palmitic acid, stearic acid, sucrose cocoate, PEG-4 dilaurate, methyl glucose sesequistearate, C11-15 pareth-3, sorbitan palmitate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, sorbityl laurate, cetearyl olivate, sorbitan olivate, ceteareth-20, isolaureth-6, behenyl glucoside, stearmide MEA, PEG-100 stearate, polysorbate 85, PEG-7, and any combination thereof.

5. The composition of claim 1, wherein the at least two cosmetically acceptable emulsifying fats are a phosphate ester and a non-ionic material.

6. The composition of claim 1, wherein the cosmetically acceptable non-ionic surfactant is selected from the group consisting of: cetearyl glucoside, decyl glucoside, cocoglucoside, lauryl glucoside, caprylyl capryl glucoside, PEG-8 oleate, polyglyceryl-3 methylglucose distearate, oleth-10, polyoxyl 10 oleyl ether, ceteth-10, PEG-8 laurate, cocoamide MEA, polysorbate 60, isolaureth-10, polysorbate 80, isosteareth-20, PEG-60 almond glycerides, PEG-20 methyl glucose sesquistearate, ceteareth-20, oleth-20, steareth-20, steareth-21, ceteth-20, C11-15 pareth-7, C11-15 pareth-9, C11-15 pareth-30, steareth-10, steareth-100, polysorbate-20, and any combination thereof.

7. The composition of claim 1, wherein the water-soluble suspending polymer is nonionic, anionic, cationic, or amphoteric polymer, a saturated or unsaturated long chain fatty acid, carboxymethylcellulose, sodium alginate, a cross-linked homopolymer of acrylic acid or of acrylamidopropanesulfonic acid or associative polymer, carbomers, hydroxyethyl cellulose, hydroxypropyl cellulose, guar gum, xanthan gum, scleroglucan gum, quaternized versions of hydroxyethyl cellulose, hydroxypropyl cellulose, guar gum, scleroglucan gum, polyquaternium-10, polyquaternium-7, polyquaternium-11, guar hydroxypropyltrimonium Chloride, hydroxypropylmethylcellulose, carboxymethylhydroxyethyl cellulose, carboxymethylhydroxypropyl guar, or any combination thereof.

8. The composition of claim 1, wherein the water-soluble suspending polymer is a carbomer or xanthan gum.

9. The composition of claim 1, wherein the multi-lamellar gel emulsion further comprises at least one agent selected from the group consisting of: a conditioning agent, an alkalizer, an antioxidant, a moisturizer, a catalyst, and any combination thereof.

10. The composition of claim 1, wherein a total HLB of the composition is about 4 to about 9.

11. The composition of claim 1, wherein a total pH of the composition is about 5 to about 12.

12. The composition of claim 1, wherein the haircolor formulation comprises an oxidation dye or a non-oxidative dye.

13. A method of making a composition of coloring hair comprising a multi-lamellar gel emulsion, wherein the multi-lamellar gel emulsion comprises:
a haircolor formulation;
at least two cosmetically acceptable emulsifying fats;
a cosmetically acceptable non-ionic surfactant;
a water-soluble suspending polymer; and
water,
wherein a cosmetically acceptable emulsifying fat content of the composition is about 0.5 wt % to about 4.0 wt %,
wherein a cosmetically acceptable non-ionic surfactant content is about 0.1 wt % to about 2 wt %, and
wherein a water content of the composition is at least 80 wt %
the method comprising:
heating a formulation comprising water to obtain heated water;
mixing the water-soluble suspending polymer and the at least two cosmetically acceptable emulsifying fats in the formulation obtained in the heating;
simultaneously cooling and homogenizing the mixed and heated formulation to obtain the multi-lamellar gel emulsion.

14. The method of claim 13, wherein the at least two cosmetically acceptable emulsifying fats are selected from the group consisting of: glycol distearate, sorbitan trioleate, propylene glycol isostearate, glycol stearate, sorbitan sisquioleate, glyceryl stearate, lecithin, sorbitan oleate, sorbitan monostearate, sorbitan stearate, sorbitan isostearate, steareth-2, oleth-2, glyceryl laurate, ceteth-2, PEG-30 dipolyhydroxystearate, glyceryl stearate, isolaureth-3, cetyl alcohol, stearyl alcohol, behenyl alcohol, cetearyl alcohol, almond oil, lanolin, apricot kernel oil, borage seed oil, canola oil, castor oil, jojoba oil, olive oil, shea butter, soybean oil, behenyl alcohol, lauryl alcohol, myristyl alcohol, palmitic acid, stearic acid, sucrose cocoate, PEG-4 dilaurate, methyl glucose sesequistearate, C11-15 pareth-3, sorbitan palmitate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, sorbityl laurate, cetearyl olivate, sorbitan olivate, ceteareth-20, isolaureth-6, behenyl glucoside, stearmide MEA, PEG-100 stearate, polysorbate 85, PEG-7, and any combination thereof.

15. The method of claim 13, wherein the at least two cosmetically acceptable emulsifying fats are a phosphate ester and a non-ionic material.

16. The method of claim 13, wherein the cosmetically acceptable non-ionic surfactant is selected from the group consisting of: cetearyl glucoside, decyl glucoside, cocoglucoside, lauryl glucoside, caprylyl capryl glucoside, PEG-8 oleate, polyglyceryl-3 methylglucose distearate, oleth-10, polyoxyl 10 oleyl ether, ceteth-10, PEG-8 laurate, cocoamide MEA, polysorbate 60, isolaureth-10, polysorbate 80, isosteareth-20, PEG-60 almond glycerides, PEG-20 methyl glucose sesquistearate, ceteareth-20, oleth-20, steareth-20, steareth-21, ceteth-20, C11-15 pareth-7, C11-15 pareth-9, C11-15 pareth-30, steareth-10, steareth-100, polysorbate-20, and any combination thereof.

17. The method of claim 13, wherein the water-soluble suspending polymer is nonionic, anionic, cationic, or amphoteric polymer, a saturated or unsaturated long chain fatty acid, carboxymethylcellulose, sodium alginate, a cross-linked homopolymer of acrylic acid or of acrylamidopropanesulfonic acid or associative polymer, carbomers, hydroxyethyl cellulose, hydroxypropyl cellulose, guar gum, xanthan gum, scleroglucan gum, quaternized versions of hydroxyethyl cellulose, hydroxypropyl cellulose, guar gum, scleroglucan gum, polyquaternium-10, polyquaternium-7, polyquaternium-11, guar hydroxypropyltrimonium Chloride, hydroxypropylmethylcellulose, carboxymethylhydroxyethyl cellulose, carboxymethylhydroxypropyl guar, or any combination thereof.

18. The method of claim 13, wherein the water-soluble suspending polymer is a carbomer or xanthan gum.

19. The method of claim 13, wherein the mixing further comprises mixing in at least one agent selected from the group consisting of a conditioning agent, an alkalizer, an antioxidant, a moisturizer, a catalyst, and any combination thereof.

20. The method of claim 13, wherein the mixing further comprises mixing in an oxidative dye.

21. The method of claim 13, wherein the mixing further comprises mixing in a non-oxidative dye.

* * * * *

UNITED STATES PATENT AND TRADEMARK OFFICE
CERTIFICATE OF CORRECTION

| | |
|---|---|
| PATENT NO. | : 11,701,308 B2 |
| APPLICATION NO. | : 16/818882 |
| DATED | : July 18, 2023 |
| INVENTOR(S) | : Jack Massoni et al. |

It is certified that error appears in the above-identified patent and that said Letters Patent is hereby corrected as shown below:

In the Specification

Column 1:
Line 43, "portion, that" should read --portion that--

Column 2:
Line 1, "and less" should read --and are less--
Line 44, "multi lamellar" should read --multi-lamellar--
Line 48, "multi lamellar" should read --multi-lamellar--
Line 56, "multi lamellar" should read --multi-lamellar--
Line 57, "consumer pleasing" should read --consumer-pleasing--
Line 60, "believed that," should read --believed that--

Column 3:
Line 1, "(gel MLE) allowing" should read --(gel MLE), allowing--
Line 35, "higher more" should read --higher, more--
Line 49, "a "maltese cross" pattern" should read --a "Maltese cross" pattern--
Line 54, "water soluble" should read --water-soluble--

Column 4:
Line 21-22, "monos-tearate" should read --mono-stearate--
Line 23-24, "dipolyhydrox-ystearate," should read --dipoly-hydroxystearate,--
Line 24, "glyceryl stearate" should be deleted
Line 28, "behenyl alcohol" should be deleted Column 5:
Line 6, "about 40,000" should read --about 40,000 cps--
Line 21, "Chloride" should read --chloride--
Line 58, "two-components" should read --two-component--
Line 66, "two component" should read --two-component--

Signed and Sealed this
Tenth Day of September, 2024

Katherine Kelly Vidal
*Director of the United States Patent and Trademark Office*

CERTIFICATE OF CORRECTION (continued)
U.S. Pat. No. 11,701,308 B2

Column 6:
Line 1, "and developer" should read --and a developer--
Line 25, "N,N-Bis(2-hydroxyethyl)" should read --N,N-bis(2-hydroxyethyl)--
Line 29, "p-methylaminphenol," should read --p-methylaminophenol--
Line 37, "3-methyl-p-aminphenol" should read --3-methyl-p-aminophenol--
Line 52, "N-(4'aminophenyl)" should read --N-(4'-aminophenyl)--
Line 56, "4-methyl-o-Phenylenediamine" should read --4-methyl-o-phenylenediamine--
Line 65, "2,4-Diaminophenol," should read --2,4-diaminophenol,--

Column 7:
Line 8, "2-ethyl amino-p-cresol," should read --2-ethylamino-p-cresol,--
Line 37, "aminoethoxy-2,4-di aminobenzene" should read --aminoethoxy-2,4-diaminobenzene--
Line 65, "3,4-Diaminophenol" should read --3,4-diaminophenol--
Line 65, "3,4-Diaminoanisole" should read --3,4-diaminoanisole--

Column 8:
Line 2, "pheneylenediamine" should read --phenylenediamine--
Line 17, "N,N'-bis(2-hydroxyethyl)-2-nitrop-phenylenediamine" should read --N,N'-bis(2-hydroxyethyl)-2-nitro-p-phenylenediamine--
Line 30, "Basic violet 2" should read --basic violet 2--
Line 35, "hydroxyanthrquinoneaminopropylmethyl" should read --hydroxyanthraquinone aminopropyl methyl--
Line 36, "hc blue 14" should read --HC blue 14--
Line 65, "alkalisilicate" should read --alkali silicate--

Column 9:
Line 6, "occlusive" should read --occlusives--
Line 10, "alpha hydroxyacids" should read --alpha hydroxy acids--
Line 21, "a water soluble salt" should read --a water-soluble salt--
Line 42, "hydrogenated," should read --hydrogenated--
Line 46-47, "myristylmeth-ylammmonium" should read --myristyl methylammonium--
Line 57, "least on" should read --least one--

Column 10:
Line 16, "monothiolgycolate" should read --monothioglycolate--
Line 21, "of, a)" should read --of: a)--
Line 26, "phase, d)" should read --phase, and d)--
Line 32, "high speed, high sheer" should read --high-speed, high-sheer--
Line 64, "fats." should read --fats.¶--
Line 64-65, "Compositions" should read --compositions--
Line 65, "two component" should read --two-component--

Column 11:
Table 1, Top Line, 2nd Column, "80-95%" should read --80%-95%--
Table 1, Line 10, 1st Column, "N,N-Bis(2-" should read --N,N-bis(2- --
Line 42, "system, will" should read --system will--

CERTIFICATE OF CORRECTION (continued)
U.S. Pat. No. 11,701,308 B2

Table 2, Line 1, 1st Column, "Lt brown" should read --Lt. brown--

Column 12:
Line 51, "fats" should read --fats.¶--
Table 3, Line 2, 1st Column, "Water Soluble" should read --Water-Soluble--

Column 13:
Table 3, Line 16, 4th Column, "0.50-4.0%" should read --0.50%-4.0%--
Line 35, "system, will" should read --system will--
Table 4, Line 1, "single component" should read --single-component--
Table 4, Line 1, 1st Column, "Lt brown" should read --Lt. brown--
Line 54, "modification," should read --modifications,--

In the Claims

Column 14:
Line 47, Claim 4 "glyceryl stearate" should be deleted
Line 51, Claim 4 "behenyl alcohol" should be deleted Column 15:
Line 19, Claim 7 "Chlo-" should read --chlo- --

Column 16:
Line 5, Claim 14 "glyceryl stearate" should be deleted
Line 9, Claim 14 "behenyl alcohol" should be deleted
Line 47, Claim 17 "Chlo-" should read --chlo- --